(12) United States Patent
Tanaka et al.

(10) Patent No.: US 6,174,711 B1
(45) Date of Patent: Jan. 16, 2001

(54) METHOD FOR PRODUCING L-ALLYSINE ACETAL

(75) Inventors: Akinori Tanaka; Masaharu Doya; Takako Uchiyama; Torakazu Tahara, all of Niigata (JP)

(73) Assignee: Mitsubishi Gas Chemical Company, Tokyo (JP)

(*) Notice: Under 35 U.S.C. 154(b), the term of this patent shall be extended for 0 days.

(21) Appl. No.: 09/351,619

(22) Filed: Jul. 12, 1999

(30) Foreign Application Priority Data

Jul. 5, 1998 (JP) .................................................. 10-200286

(51) Int. Cl.$^7$ ........................... C12P 13/06; C12P 13/00; C12P 13/02
(52) U.S. Cl. ........................... 435/128; 435/106; 435/129
(58) Field of Search ..................................... 435/106, 128, 435/129

(56) References Cited

U.S. PATENT DOCUMENTS

| | | |
|---|---|---|
| 5,508,272 | 4/1996 | Robl . |
| 5,627,278 | 5/1997 | Robl . |
| 5,670,699 | 9/1997 | Robl . |
| 5,672,599 | 9/1997 | Robl . |
| 5,756,832 | 5/1998 | Robl . |

FOREIGN PATENT DOCUMENTS

| | | |
|---|---|---|
| 905257 | 3/1999 | (EP) . |
| 7-48259 | 2/1995 | (JP) . |

OTHER PUBLICATIONS

Computer JPAB abstract Uragami et al JP363157990A Jun. 30, 1988.*
Bioorganic & Medicinal Chemistry, vol. 3, No. 9, pp. 1237–1240; 1945.

"Chemical Synthesis of Allysine Ethylene Acetal and Conversion in Situ into 1–Piperideine–6–carboxylic Acid–Key Intermediate of the Alpha–Aminoadipic Acid For Beta–L–catam Antibiotics Biosynthesis", *Bioorganic & Medicinal Chemistry,* vol. 3, No. 9, pp. 1237–1240; 1945.

"Alpha–Amino Acid Amides—A convenient Systhesis", *Journal of Organic Chemistry,* vol. 27, 1962, pp. 98–802.

* cited by examiner

*Primary Examiner*—Herbert J. Lilling
(74) *Attorney, Agent, or Firm*—Kilpatrick Stockton LLP

(57) ABSTRACT

A method for producing L-allysine acetal represented by general formula (II), comprising reacting D,L-allysinamide acetal represented by general formula (I) with cells of microorganism or treated cell product having an activity of stereoselectively hydrolyzing L-allysinamide acetal,

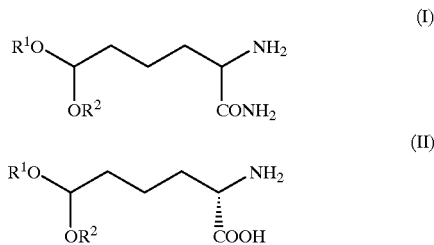

wherein $R^1$ and $R^2$, which may be the same or different, each independently represent a lower alkyl group, or $R^1$ and $R^2$ are combined to form an alkylene group represented by $[CH_2]_n$, and n is 2 to 3. D,L-allysinamide acetal represented by general formula (I) is also in the scope of the invention. According to the present invention, L-allysine acetal useful as a raw material for medicine can be produced in a smaller number of steps at low costs.

6 Claims, No Drawings

METHOD FOR PRODUCING L-ALLYSINE ACETAL

BACKGROUND OF THE INVENTION

1. Field of the Invention

The present invention relates to a method for producing L-allysine acetal. More particularly, the present invention relates to a method of biochemical asymmetric hydrolysis of D,L-allysinamide acetal to produce corresponding L-allysine acetal. L-Allysine acetal is an important substance as an intermediate for producing medicines.

2. Description of the Related Art

Hitherto known methods for the production of L-allysine acetal include, for example, the method described in Japanese Patent Application Laid-open No. Hei 7-48259. This method comprises the steps of stereoselectively hydrolyzing N-acetyl-D,L-hydroxynorleucine, which has been derived by a two-step reaction from diethyl acetamidomalonate, with a swine liver acylase to obtain L-hydroxynorleucine, converting an amino group of the L-hydroxynorleucine to phthalimide, and a carboxyl group of the L-hydroxynorleucine to its methyl ester for protection, converting a hydroxyl group thereof to aldehyde by Swern oxidation, and further converting aldehyde thereof to dimethyl acetal, followed by deprotecting the phthalimide to obtain L-allysine dimethyl acetal as methyl ester. The method involves many steps, gives low yield, and requires expensive reagents, so that it cannot be said to be industrially advantageous.

Besides this, Bioorganic & Medicinal Chemistry, Vol.3, 1237–1240 (1995) describes a method for producing D,L-allysine ethylene acetal from 3,4-dihydro-2H-pyrane by 8-step reaction. This method also involves many steps, gives low yield, and requires further expensive reagents, so that it cannot be said to be industrially advantageous. The literature describes only the method for producing racemic modification but fails to describe optically active substance of L-allysine acetal.

SUMMARY OF THE INVENTION

An object of the present invention is to solve the above-mentioned problems encountered by the prior art and provide a method for producing L-allysine acetal by less number of steps at low cost.

The present inventors have made intensive research for a method for producing L-allysine acetal in a small number of steps inexpensively and as a result they have been successful in the synthesis of D,L-allysinamide acetal, a novel compound, and have found that the D,L-allysinamide acetal is biochemically hydrolyzed by the enzymatic action of a microorganism to give L-allysine acetal, thus reaching the present invention.

(1) That is, the present invention relates to a method for producing L-allysine acetal represented by general formula (II), comprising reacting D,L-allysinamide acetal represented by general formula (I) with cells of microorganism or treated cell product having an activity of stereoselectively hydrolyzing L-allysinamide acetal,

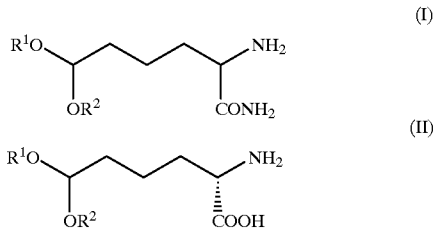

wherein $R^1$ and $R^2$, which may be the same or different, each independently represent a lower alkyl group, or $R^1$ and $R^2$ are combined to form an alkylene group represented by $[CH_2]_n$, and n is 2 to 3.

(2) Further, the present invention relates to a method for producing L-allysine acetal as described in (1) above, wherein after the cells of microorganism or treated cell product is reacted on D,L-allysinamide acetal, unreacted D-allysinamide acetal is heated in the presence of a strongly basic substance to racemize it to obtain D,L-allysinamide acetal, which is used again as a raw material.

(3) Further, the present invention relates to a compound, D,L-allysinamide acetal, which is used as a raw material for the reaction described in (I) and to a method for producing it.

According to the present invention, L-allysine acetal useful as a raw material for producing medicine can be produced in a smaller number of steps at low cost.

DETAILED DESCRIPTION OF THE INVENTION

Hereafter, the present invention will be described in detail.

A reaction scheme of the present invention is shown below, which illustrates that a novel compound D,L-allysinamide acetal (general formula (I)) is synthesized from a known product of glutaraldehyde monoacetal (general formula (III)) as a starting material and D,L-allysinamide acetal is then stereoselectively hydrolyzed using cells of microorganism to produce L-allysine acetal (general formula (II)), wherein D-allysinamide acetal which remains without undergoing stereoselective hydrolysis is racemized to return to D,L-allysinamide acetal as a raw material.

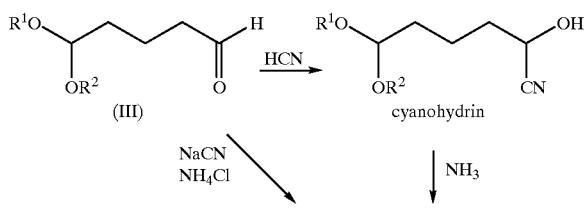

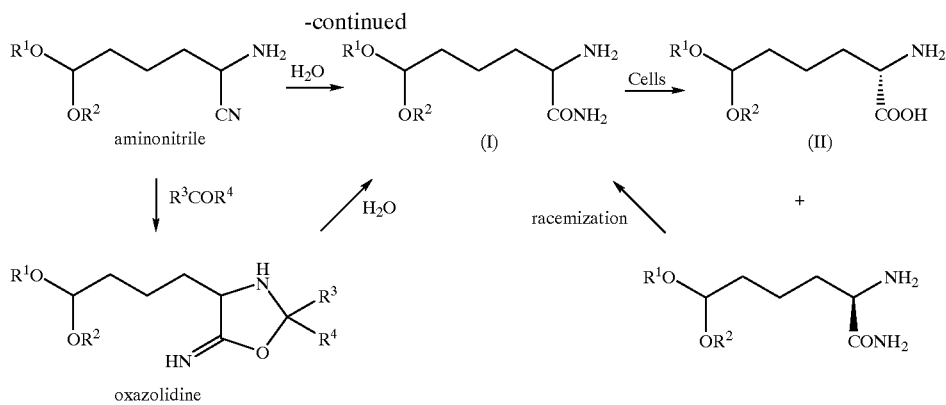

aminonitrile → (I) → (II)

oxazolidine

Hereafter, the present invention will be described in accordance with the reaction scheme.

Glutaraldehyde monoacetal represented by general formula (III) is synthesized by known methods, for example, by monoacetalization of glutaraldehyde (Japanese Patent Application Laid-open No. Sho 48-39416) as well as by oxidation of 5,5-dimethoxy-1-pentanol (J. Am. Chem. Soc., Vol. 104, 1033–1041, (1982)) and hydroformylation of 4,4-diethoxy-1-butene (J. Am. Chem. Soc., Vol. 115, 2066–2068, (1993)) and the like.

D,L-α-aminonitrile (indicated as aminonitrile in the above-mentioned reaction scheme) is synthesized by Strecker reaction, in which glutaraldehyde monoacetal is reacted with hydrocyanic acid and ammonia, or with cyanide and ammonium salt. The method of Strecker reaction includes a 2-step method in which first glutaraldehyde monoacetal is reacted with hydrocyanic acid to produce cyanohydrin and then the cyanohydrin is reacted with ammonia to produce aminonitrile, and a 1-step method in which glutaraldehyde monoacetal is reacted with cyanide and ammonium salt to produce aminonitrile.

The reaction conditions for the step of reacting glutaraldehyde monoacetal with hydrocyanic acid to produce cyanohydrin are not limited particularly but usually the reaction is carried out in the presence of a basic catalyst at reaction temperature of 0 to 20° C. The reaction conditions for the step of reacting cyanohydrin with ammonia to produce D,L-α-aminonitrile are not limited particularly but usually the reaction is carried out using 5- to 10-fold molar amount of ammonia based on cyanohydrin and usually at temperature of 20 to 80° C. because reaction at too low temperature may result in slow reaction rate and too high temperature may result in the decomposition product.

The reaction conditions for the step of reacting glutaraldehyde with cyanide and ammonium salt to produce aminonitrile in one step are not limited particularly but the reaction is carried out at reaction temperature of 0 to 50° C. The cyanide is preferably alkali cyanide, of which potassium cyanide and sodium cyanide are particularly preferred. The ammonium salt is preferably ammonium chloride.

There are two methods for producing D,L-allysinamide acetal represented by general formula (I) from D,L-α-aminonitrile. One is a method in which D,L-α-aminonitrile is partially hydrolyzed and the other is a method in which D,L-α-aminonitrile is reacted with a ketone represented by $R^3COR^4$ (wherein $R^3$ and $R^4$ are independently a lower alkyl group) to produce oxazolidine and then the oxazolidine is hydrolyzed.

The reaction conditions when D,L-α-aminonitrile is partially hydrolyzed are not limited particularly but usually the partial hydrolysis is carried out in the presence of a basic catalyst and ketone in aqueous solution at reaction temperature of 0 to 30° C.

The reaction conditions when D,L-allysinamide acetal is produced via oxazolidine are not limited particularly but usually the oxazolidine synthesis is carried out in the presence of a basic catalyst and using about 1- to 5-fold molar amount of ketone based on aminonitrile and at reaction temperature of about −10 to 50° C., preferably 0 to 30° C. and then the obtained oxazolidine is hydrolyzed in aqueous solution at reaction temperature of about 0 to 50° C.

The method for producing D,L-allysinamide acetal in this manner is advantageous in point that it can be easily produced from aldehydes, hydrocyanic acid and ammonia which are widely used as industrial raw materials.

In the present invention, typical examples of D,L-allysinamide acetal represented by general formula (I) include D,L-allysinamide dimethyl acetal (D,L-2-amino-6,6-dimethoxyhexanamide), D,L-allysinamide diethyl acetal (D,L-2-amino-6,6-diethoxyhexanamide), D,L-allysinamide ethylene acetal (D,L-2-amino-6,6-ethylenedioxyhexanamide) and the like. The D,L-allysinamide acetal represented by general formula (I) are not limited particular in its production method, quality or the like.

In the present invention, the cells of microorganism used in the biochemical hydrolysis of D,L-allysinamide acetal may be any microbial cell that has an activity of stereoselectively hydrolyzing L-allysinamide acetal corresponding to the targeted L-allysine acetal. Such a microorganism includes bacteria belonging to the genera Pseudomonas, Cryptococcus, Lodderomyces, Rhodosporidium, Mycoplana, Pachysolen and the like but is not limited to these. Specific examples of the bacteria include *Mycoplana bullata* NCIB 9440, *Pseudomonas rosea* NCIB 10605, *Cryptococcus laurentii* ATCC 18803, *Lodderomyces elogisporus* IFO 1676, *Rhodosporidium toruloides* IFO 0871, and *Pachysolen tannophilus* IFO 1007.

Culture of these microorganisms is carried out using medium containing usual assimilable carbon sources, nitrogen sources, inorganic salts essential to each microorganism, nutrients or the like. However, in order to obtain high enzymatic activity, it is effective to add D,L-α-amino acid amide in the medium in advance. In this case, it is preferred to use D,L-allysinamide acetal corresponding to the targeted L-allysine acetal as the D,L-α-amino acid amide to be added. However, it may be D,L-α-amino acid amide usually used, for example, D,L-alanine amide, D,L-valine amide or the like and is not limited particularly. Upon culturing, pH is in the range of 4 to 10 and the temperature is 20 to 50° C. The culture is carried out aerobically for about 1 day to 1 week. The cultured microorganism in this manner is used in reaction in the form of culture broth, separated cell, disrupted cell, or purified enzyme. Alternatively, the cell or enzyme may be immobilized for use by known method. The treated cell product means a material obtained by treating cells, that is, the above-mentioned disrupted cell product, purified enzyme, immobilized cell or enzyme.

The conditions for the biochemical hydrolysis reaction of D,L-allysinamide acetal are as follows. The concentration of D,L-allysinamide acetal in reaction mixture is 1 to 40 wt %, the amount of usage of cells of microorganism and/or treated microbial cell product is in the range of 0.005 to 3 by weight ratio based on D,L-allysinamide acetal as dry cell, the reaction temperature is in the range of 20 to 70° C., and the pH is in the range of 5 to 13.

The L-allysine acetal produced by the biochemical hydrolysis reaction from D,L-allysinamide acetal can be easily separated from the reaction mixture after completion of the reaction by a method which comprises the steps of removing the cells of microorganism and/or treated cell products by usual solid-liquid separation means, for example, centrifugation or filtration membrane, concentrating the obtained liquid under reduced pressure, adding an organic solvent to the concentrate to precipitate L-allysine acetal and then collecting the precipitated L-allysine acetal by filtration. Alternatively another method may be used, which comprises the steps of removing the cells of microorganism and/or treated cell products, distilling off water from the obtained liquid under reduced pressure, adding organic solvent to the residual solids to dissolve unreacted D-allysinamide acetal, and then collecting insoluble L-allysine acetal by filtration. In this case, the organic solvent added in order to precipitate L-allysine acetal or dissolve unreacted D-allysinamide acetal is not limited particularly so long as it has low solubility for L-allysine acetal and high solubility for unreacted D-allysinamide acetal. Alcohols such as ethanol, 2-propanol, 2-methyl-1-propanol, 1-butanol and 2-butanol are preferably used. Isolating L-allysine acetal can be also carried out by a method which comprises the steps of separating cells of microorganism and/or treated cell products from the reaction mixture after completion of the reaction, removing unreacted D-allysinamide acetal by solvent extraction from the obtained reaction mixture and then separating L-allysine acetal from the residual liquid by crystallization or the like. In this case, the solvent for extracting D-allysinamide acetal includes non-polar solvent, for example, hexane, benzene, toluene and xylene. Besides this, there is a useful method in which after removing cells of microorganism and/or treated microbial cell products from the reaction mixture after completion of the reaction, L-allysine acetal alone can be separated and recovered by ion exchange electrodialysis.

The unreacted D-allysinamide acetal can be easily recovered by a method of concentrating the liquid after L-allysine acetal is removed from the biochemical hydrolysis reaction mixture after completion of the reaction of D,L-allysinamide acetal as discribed above or by a method of solvent extraction from the reaction mixture after completion of the reaction after the cells of microorganism and/or treated microbial cell products are removed. The recovered D-allysinamide acetal is easily racemized to D,L-allysinamide acetal by heating in the presence of a strongly basic substance, so that it can be used again as a raw material for biochemical hydrolysis reaction. As the D-allysinamide acetal used in the racemization reaction of D-allysinamide acetal, there may be used the D-allysinamide acetal recovered from the biochemical hydrolysis reaction mixture after copletion of the reaction of D,L-allysinamide acetal as discribed above as it is or purified by recrystallization or the like, if necessary.

The strongly basic substance used in the racemization reaction of D-allysinamide acetal may be any organic or inorganic strongly basic substance and typical examples thereof include organic quaternary ammonium compounds such as tetramethylammonium hydroxide and tetraethylammonium hydroxide and alkali metal compounds such as sodium hydroxide, potassium hydroxide, sodium methylate, sodium ethylate, sodium amide and sodium hydride, and alkaline earth metal compounds such as barium hydroxide. It is also possible to add substances which are converted to the above-mentioned strongly basic substances in the reaction system, for example, elemental alkali metals such as sodium and potassium, and elemental alkaline earth metals such as barium.

The amount of usage of the strongly basic substance is in a proportion of 0.001 to 0.5 mole, preferably 0.01 to 0.1 mole, per mole of D-allysinamide acetal.

Although the racemization reaction of D-allysinamide acetal may be carried out without using solvent, use of solvent can make the reaction temperature decrease and hence the possibility that by-products will be produced lower and it is more advantageous. In this case, the solvent used may be any solvent so long as it is inactive to both D-allysinamide acetal and the strongly basic substance and includes hydrocarbons such as hexane, heptane, cyclohexane, benzene, toluene and xylene, alcohols such as 2-propanol, 2-methyl-1-propanol, 2-butanol, 1-butanol, 1-pentanol, isobutyronitrile and the like. The amount of usage of solvent is not limited particularly but in practice it does not have to be larger than 100-fold based on the weight of D-allysinamide acetal and 1- to 20-fold weight is preferred.

The moisture in the racemization reaction mixture is preferably as little as possible but about 1 wt % or less causes almost no problem and 0.1 wt % or less causes practically no problem. The racemization temperature is 20 to 200° C., preferably 50 to 150° C. The racemization reaction is carried out usually under atmospheric pressure but may be performed also under reduced pressure or under increased pressure.

The method for separating and recovering the resulting D,L-allysinamide acetal after completion of the racemization reaction includes, for example, a method of removing the solvent under reduced pressure, cooling the reaction mixture to precipitate crystals, and then separating and recovering it by usual solid-liquid separation operation such as filtration or centrifugation, or a method of adding water to the reaction mixture of racemization after completion of the reaction to elute D,L-allysinamide acetal in aqueous phase and circulating it to the biochemical hydrolysis step as it is or after adjusting pH. The latter method is more reasonable for industrial purposes.

By racemizing D-allysinamide acetal to D,L-allysinamide acetal and circulating it to the biochemical hydrolysis reaction system in this manner, the total amount of D,L-allysinamide acetal can be converted to L-allysine acetal.

The method of the present invention specifically enables production of L-allysine acetal such as L-allysine dimethyl acetal, L-allysine diethyl acetal and L-allysine ethylene acetal.

BEST MODE FOR CARRYING OUT THE INVENTION

Hereafter, the present invention will be described more specifically by examples. However, the present invention is not limited thereto.

EXAMPLE 1

Production of D,L-allysinamide Acetal From Glutaraldehyde Monoacetal (a) Production of D,L-6,6-Ethyelendioxy-2-hydroxyhexanenitrile In a four-necked 200-ml flask equipped with a stirrer, a thermometer, a reflux condenser, and a dropping funnel, 35 g of methyl t-butyl ether was charged and then cooled to 5° C., and 8.0 g (0.30 mol) of hydrocyanic acid was added thereto. To it 0.6 g of triethylamine was added with stirring and 33.0 g (0.23 mol) of 5,5-ethylenedioxypentanal was dropped from the dropping funnel in portions slowly over about 20 minutes so that the temperature of reaction mixture could not exceed 20° C. Further, after stirring the reaction mixture at 20° C. for 2 hours, the reaction mixture containing crude D,L-6,6-ethylenedioxy-2-hydroxyhexanenitrile was supplied as it was to the subsequent amination step.

(b) Production of D,L-2-amino-6,6-ethylenedioxyhexanenitrile

In a 200-ml pressure resistant vessel, 76 g of the reaction mixture containing crude D,L-6,6-ethylenedioxy-2-hydroxyhexanenitrile obtained in (a) above was charged. Once it was cooled to −20° C., 39.1 g (2.3 mol) of liquid ammonia was added. Thereafter the resulting mixture was shaken in a water bath at 40° C. for 2 hours and then left to stand at room temperature for 15 hours. After returning the inner pressure of reaction system to atmospheric pressure by purging of ammonia, the reaction mixture was transferred to a 200-ml egg plant type flask, followed by removing excessive ammonia using an evaporator to obtain 40.0 g of crude D,L-2-amino-6,6-ethylenedioxyhexanenitrile as brown only product.

(c) Production of D,L-allysinamide Ethylene Acetal (D,L-2-amino-6,6-ethyelendioxyhexanamide)

In a 300-ml four-necked flask equipped with a stirrer, a thermometer and a pH electrode 40 g of distilled water and 40 g of acetone were charged and then cooled to 5° C. To this 39.0 g of the crude D,L-2-amino-6,6-ethylenedioxyhexanenitrile obtained in (b) above was added and further 2.5 g of aqueous 40% sodium hydroxide solution (1.0 g, 0.025 mol as sodium hydroxide) was added under ice cooling while stirring. After the addition of aqueous 40% sodium hydroxide solution, the temperature of the reaction mixture was elevated to 15° C. After stirring the reaction mixture for 10 hours, 5.0 g of 18% hydrochloric acid (0.9 g, 0.025 mol as hydrochloric acid) was added. Thereafter water and acetone were distilled off using an evaporator. The residue (45.7 g) was dissolved in 100 ml of dimethyl carbonate and insoluble solids were removed by filtration. After the solvent in the filtrate was concentrated by an evaporator, the resultant was cooled to 5° C. to precipitate white crystals of D,L-allysinamide ethylene acetal, which crystals were collected by filtration. The obtained crystals after drying weighed 35.0 g (0.19 mol) and yield based on 5,5-ethylenedioxypentanal was 81 mol %.

Next, the melting point, elemental analysis data, IR spectrum, $^1$H-NMR spectrum, and $^{13}$C-NMR spectrum of the obtained D,L-allysinamide ethylene acetal are described below.

1) Melting point: 65–67° C.

2) Elemental analysis data: $C_8H_{16}N_2O_3$ (MW 188.23)

| Calculated (%) | C51.05 | H8.57 | N14.88 |
|---|---|---|---|
| Measured (%) | C50.82 | H8.78 | N14.91 |

3) IR spectrum (vmax value, cm$^{-1}$): (KBr)
   3352, 3296, 2953, 1674, 1606, 1416, 1142, 939

4) $^1$H-NMR spectrum (δvalue, ppm): (CDCl$_3$, internal standard: TMS)
   1.63 (m, 6H), 1.84 (m, 2H), 3.34 (m, 1H), 3.89 (m, 4H), 4.86 (m, 1H), 6.29 (br, 1H), 7.08 (br, 1H)

5) $^{13}$C-NMR spectrum (δvalue, ppm): (CDCl$_3$, internal standard: TMS)
   20.3, 33.6, 35.0, 55.1, 64.8, 104.2, 178.4

EXAMPLE 2

Production of L-allysine Acetal From D,L-allysinamide Acetal (1)

a) Production of L-allysine Ethylene Acetal

A medium was prepared having the following composition and 200 ml of the medium was charged in a 1-liter Erlenmeyer flask. After it was autoclaved, *Mycoplana bullata* NCIB 9440 was inoculated thereto and shaking culture was practiced at 30° C. for 48 hours.

Composition of medium (pH 7.0)

| Glucose | 10 g |
|---|---|
| Polypeptone | 5 g |
| Yeast extract | 5 g |
| KH$_2$PO$_4$ | 2 g |
| MgSO$_4$.7H$_2$O | 0.4 g |
| FeSO$_4$.7H$_2$O | 0.01 g |
| MnCl$_2$.4H$_2$O | 0.01 g |
| D,L-Valine amide | 5 g |
| Distilled water | 1 liter |

When the culture was completed, the cell concentration of culture was 5 g/kg. Live cells corresponding to 0.5 g of dry cells was obtained from 100 g of the culture. The live cells were suspended in 100 ml of distilled water and it was charged in a 1-liter Erlenmeyer flask, to which 5.0 g (27 mmol) of D,L-2-amino-6,6-ethylenedioxyhexanamide was added, followed by hydrolysis reaction at 40° C. for 5 hours with shaking. The pH of the reaction solution was 9.4.

After the reaction, the cells of microorganism were removed from the reaction mixture by centrifugation. After water was removed using an evaporator under reduced pressure, 100 ml of 2-propanol was added to dissolve unreacted D-2-amino-6,6-ethylenedioxyhexanamide and then insoluble L-allysine ethylene acetal was collected by filtration as white solids. The obtained solids weighed 2.4 g (13 mmol) after drying and yield based on D,L-2-amino-6,6-ethylenedioxyhexanamide was 48 mol % and based on L-2-amino-6,6-ethylenedioxyhexanamide 95 mol %. Further, liquid chromatography analysis of the produced L-allysine ethylene acetal using a chiral column for optical resolution (CHIRALPAK WH, manufactured by Daicel Chemical Industry) showed that optical purity was 99% e.e. or more.

Next, the melting point, elemental analysis data, IR spectrum, $^1$H-NMR spectrum, and $^{13}$C-NMR spectrum of the obtained L-allysine ethylene acetal are described below.

1) Melting point: 217–218° C.
2) Elemental analysis data: $C_8H_{15}NO_4$ (MW 189.21)

| | | | |
|---|---|---|---|
| Calculated (%) | C50.78 | H7.99 | N7.40 |
| Measured (%) | C50.65 | H8.07 | N7.22 |

3) IR spectrum (vmax value, $cm^{-1}$): (KBr)
   2950, 2873, 1581, 1514, 1444, 1408, 1145, 1061, 945
4) $^1$H-NMR spectrum (δvalue, ppm): ($D_2O$, internal standard: TMS-PS)
   1.3–2.1 (m, 6H), 3.69 (t, J=5.9 Hz, 1H), 3.92 (m, 4H), 4.90 (t, J=4.5 Hz, 1H)
5) $^{13}$C-NMR spectrum (δvalue, ppm): ($D_2O$, internal standard: TMS-PS)
   21.7, 32.9, 34.8, 57.3, 67.2, 106.3, 177.0

(b) Recovery of D-2-amino-6,6-ethylenedioxyhexanamide

The solvent was distilled off using an evaporator under reduced pressure from the filtrate after the solids of L-allysine ethylene acetal were filtered off. Fifty ml of diisopropyl ether was added thereto, followed by collection of insoluble solids by filtration to obtain unreacted D-2-amino-6,6-ethylenedioxyhexanamide as white solids. The solids weighed was 2.2 g (12 mmol) after drying. Recovery based on D,L-2-amino-6,6-ehtylenedioxyhexanamide was 44 mol % and based on D-2-amino-6,6-ethylenedioxyhexanamide 88 mol %. Liquid chromatography analysis of the recovered D-2-amino-6,6-ethylenedioxyhexanamide using a chiral column for optical resolution (CROWNPAK CR, manufactured by Daicel Chemical Industry) showed that optical purity was 99% e.e. or more.

(c) Racemization of D-2-amino-6,6-ethylenedioxyhexanamide

D-2-amino-6,6-ethylenedioxyhexanamide (1.0 g (5.3 mmol)) was dissolved in 10 ml of 2-methyl-1-propanol and 0.02 g (0.5 mmol) of sodium hydroxide was added thereto. Then the mixture was stirred at 110° C. for 30 minutes.

After completion of the reaction, the reaction mixture was cooled and diisopropyl ether was added thereto to precipitate solids, which were collected by filtration to obtain D,L-2-amino-6,6-ethylenedioxyhexanamide. The solids weighed 0.98 g (5.2 mmol) after drying and recovery was 98 mol %.

Liquid chromatography analysis of the solids using a chiral column for optical resolution (CROWNPAK CR) showed that racemization ratio of D-2-amino-6,6-ethylenedioxyhexanamide was 98%. The racemization ratio was calculated as follows.

Racemization ratio (%) = L-amide / (L-amide + D-amide) × 2 × 100

The racemization ratio of 100% means that L-allysinamide acetal and D-allysinamide acetal are in equivalent amounts.

EXAMPLE 3

Production of L-allysine Acetal From D,L-allysinamide Acetal (2)

Live cells corresponding to 0.1 g of dry cells centrifuged from 20 g of the culture medium in Example 2 were suspended in 20 ml of distilled water and the suspension was charged in a 100-ml Erlenmeyer flask, to which 0.5 g (2.7 mmol) of D,L-2-amino-6,6-ethylenedioxyhexanamide racemized and recovered in Example 2 and 0.5 g (2.7 mmol) of new D,L-2-amino-6,6-ethylenedioxyhexanamide were added. Then it was shaken at 40° C. for 5 hours to practice hydrolysis reaction. The pH of the reaction solution was 9.5.

After the reaction was completed, the post-treatments were carried out in the same manner as in Example 2 to obtain L-allysine ethylene acetal as white solids. The obtained solids weighed 0.47 g (2.5 mmol) after drying and yield based on newly added D,L-2-amino-6,6-ethylenedioxyhexanamide was 93 mol %. Further, liquid chromatography analysis of the produced L-allysine ethylene acetal using a chiral column for optical resolution (CHIRALPAK WH) showed that optical purity was 99% e.e. or more.

What is claimed is:

1. A method for producing L-allysine acetal represented by general formula (II), comprising reacting D,L-allysinamide acetal represented by general formula (I) with cells of microorganism or treated cell product having an activity of stereoselectively hydrolyzing L-allysinamide acetal,

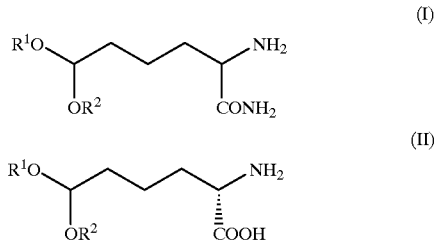

wherein $R^1$ and $R^2$, which may be the same or different, each independently represent a lower alkyl group, or $R^1$ and $R^2$ are combined to form an alkylene group represented by $[CH_2]_n$, and n is 2 to 3.

2. The method of claim 1, wherein after the cells of microorganism or treated cell product is reacted on D,L-allysinamide acetal, unreacted D-allysinamide acetal is heated in the presence of a strongly basic substance to racemize it to obtain D,L-allysinamide acetal, which is used again as a raw material.

3. The method of claim 1 or 2, which further comprises the steps of deriving aminonitrile from gultaraldehyde monoacetal represented by general formula (III);

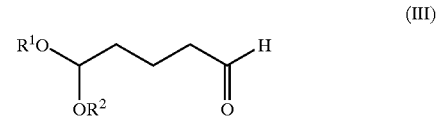

wherein $R^1$ and $R^2$, which may be the same or different, each independently represent a lower alkyl group, or $R^1$ and $R^2$ are combined to form an alkylene group represented by $[CH_2]_n$, and n is 2 to 3; by reacting the gultaraldehyde monoacetal with hydrocyanic acid and ammonia, or with cyanide and ammonia salt, and obtaining D,L-allysinamide acetal represented by general formula (I) by partially hydrolyzing the aminonitrile with an alkali.

4. The method of claim 1 or 2, which further comprises the steps of deriving an aminonitrile from gultaraldehyde monoacetal represented by general formula (III);

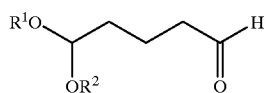

(III)

wherein $R^1$ and $R^2$, which may be the same or different, each independently represent a lower alkyl group, or $R^1$ and $R^2$ are combined to form an alkylene group represented by $[CH_2]_n$, and n is 2 to 3; by reacting the gultaraldehyde monoacetal with hydrocyanic acid and ammonia, or with cyanide and ammonia salt; and obtaining D,L-allysinamide acetal represented by general formula (I) by reacting said aminonitrile with ketone to obtain an oxazolidine and hydrolyzing the oxazolidine with an alkali.

5. The method of claim 1, wherein the microorganism is selected from the group consisting of the genera Pseudomonas, Cryptococcus, Lodderomyces, Rhodosporidium, Mycoplana and Pachysolen.

6. The method of claim 1, wherein the microorganism is *Mycoplana bullata*.

* * * * *